US012582428B2

(12) United States Patent
Hurley et al.

(10) Patent No.: US 12,582,428 B2
(45) Date of Patent: Mar. 24, 2026

(54) CLAMP AND CABLE

(71) Applicant: Brook Orthopaedics Ltd, County Galway (IE)

(72) Inventors: Conor Hurley, County Galway (IE); Robert Hurley, County Galway (IE); Patrick Hurley, County Galway (IE)

(73) Assignee: Brook Orthopaedics Ltd, County Galway (IE)

( * ) Notice: Subject to any disclaimer, the term of this patent is extended or adjusted under 35 U.S.C. 154(b) by 696 days.

(21) Appl. No.: 17/266,899

(22) PCT Filed: Aug. 6, 2019

(86) PCT No.: PCT/EP2019/071146
§ 371 (c)(1),
(2) Date: Feb. 8, 2021

(87) PCT Pub. No.: WO2020/030656
PCT Pub. Date: Feb. 13, 2020

(65) Prior Publication Data
US 2022/0110648 A1 Apr. 14, 2022

(30) Foreign Application Priority Data
Aug. 8, 2018 (GB) ..................................... 1812903

(51) Int. Cl.
A61B 17/28 (2006.01)
A61B 5/00 (2006.01)
(Continued)

(52) U.S. Cl.
CPC ........ *A61B 17/282* (2013.01); *A61B 17/0482* (2013.01); *A61B 17/8861* (2013.01);
(Continued)

(58) Field of Classification Search
CPC .............. A61B 17/282; A61B 17/0482; A61B 17/8861; A61B 17/8866; A61B 17/82;
(Continued)

(56) References Cited

U.S. PATENT DOCUMENTS 4,966,600 A * 10/1990 Songer ............... A61B 17/8861
606/103
5,188,636 A * 2/1993 Fedotov .............. A61B 17/1114
606/139
(Continued)

FOREIGN PATENT DOCUMENTS

CN 201617941 U 11/2010
CN 103932768 A 7/2014
(Continued)

*Primary Examiner* — Marcela I. Shirsat
(74) *Attorney, Agent, or Firm* — Morse, Barnes-Brown & Pendleton, P.C.; Martin Z. Zhang; Russell L. Widom

(57) ABSTRACT

A bone clamp (1, 200, 300) for use in fixation of a fractured bone, or prevention of fracture of a bone, the clamp (1, comprising a pair of handles (2a, 2b) joined together at a pivot point (5), the handles (2a, 2b) each having an arcuate jaw (4a 4b), the arcuate jaws (4a, 4b) comprising a first end (7a, 7b) having an opening at a proximal end (12a, 12b) of the jaw (4a, 4b) in communication with a second end (8a, 8b) having an opening at a distal end (14a, 14b) of the jaw (4a, 4b), the first end (7a, 7b) and second end (8a, 8b) in communication via a channel (6a, 6b), in which the channel (6a, 6b) is configured to accommodate a cable, a wire, a suture, a band or other suitable flexible material, and wherein the channel (6a, 6b) is an open channel.

20 Claims, 7 Drawing Sheets

(51) Int. Cl.

| | |
|---|---|
| *A61B 10/06* | (2006.01) |
| *A61B 17/04* | (2006.01) |
| *A61B 17/16* | (2006.01) |
| *A61B 17/22* | (2006.01) |
| *A61B 17/29* | (2006.01) |
| *A61B 17/44* | (2006.01) |
| *A61B 17/82* | (2006.01) |
| *A61B 17/84* | (2006.01) |
| *A61B 17/88* | (2006.01) |
| *B25B 7/00* | (2006.01) |

(52) U.S. Cl.

CPC ........ *A61B 17/8866* (2013.01); *A61B 5/6838* (2013.01); *A61B 5/6884* (2013.01); *A61B 10/06* (2013.01); *A61B 17/0483* (2013.01); *A61B 17/0487* (2013.01); *A61B 17/1606* (2013.01); *A61B 17/22031* (2013.01); *A61B 2017/2808* (2013.01); *A61B 17/2812* (2013.01); *A61B 2017/2904* (2013.01); *A61B 2017/2915* (2013.01); *A61B 2017/2926* (2013.01); *A61B 2017/2945* (2013.01); *A61B 17/44* (2013.01); *A61B 17/82* (2013.01); *A61B 17/842* (2013.01); *B25B 7/00* (2013.01); *Y10T 29/539* (2015.01)

(58) Field of Classification Search

CPC ... A61B 17/842; A61B 17/0487; A61B 17/30; A61B 17/0483; A61B 17/28; A61B 17/1606; A61B 17/22031; A61B 17/44; A61B 17/2804; A61B 17/2812; A61B 5/6838; A61B 5/6884; A61B 10/06; A61B 2017/2926; A61B 2017/1125; A61B 2017/2808; A61B 2017/2825; A61B 2017/2829; A61B 2017/2904; A61B 2017/2915; A61B 2017/2945; Y10T 29/539; B21F 15/00; B25B 7/00

USPC .......................... 606/74, 324, 205, 207, 209

See application file for complete search history.

(56) References Cited

U.S. PATENT DOCUMENTS

| | | | | |
|---|---|---|---|---|
| 5,222,962 | A | * | 6/1993 | Burkhart ............ A61B 17/0469 606/147 |
| 6,086,596 | A | | 7/2000 | Durham |
| 2005/0192474 | A1 | * | 9/2005 | Vanden Hoek ....... A61F 2/2481 606/205 |
| 2007/0043377 | A1 | | 2/2007 | Fenandez |

FOREIGN PATENT DOCUMENTS

| | | | |
|---|---|---|---|
| EP | 0238219 | A1 | 9/1987 |
| EP | 3116424 | A2 | 1/2017 |
| FR | 2777448 | A1 | 10/1999 |
| FR | 2977787 | A1 | 1/2013 |
| WO | WO-8806022 | A1 | 8/1988 |

* cited by examiner

CLAMP AND CABLE

CROSS REFERENCE TO RELATED APPLICATIONS

This application is the National Stage of International Application No. PCT/EP2019/071146, filed on Aug. 6, 2019, which claims priority to Great Britain Application No. 1812903.1, filed on Aug. 8, 2018. The contents of both applications are hereby incorporated by reference in their entirety.

FIELD OF THE INVENTION

The present invention relates to an instrument for passing a cable or wire around a bone for fixation of a fracture or to prevent fracture. More specifically, the invention relates to a bone reduction clamp with an integrated cable passer for passing a cable (or a suture, a wire, a device and the like) around a bone, and a cable or wire for use with the bone reduction clamp.

BACKGROUND TO THE INVENTION

Cerclage tools, including cable passers, are used when treating, for example, femoral fractures, hip fractures, lower leg fractures, arm fractures, forearm fractures, hand fractures, foot fractures, clavicle fractures, spinal fractures, patella fractures, amongst other orthopaedic surgeries. Most of the cable passers in the prior art are designed with a curvature to partially encircle the bone shaft and are formed from a rigid material and are large, cumbersome medical instruments. During insertion, and/or preparation for insertion, the cable passer and other tunnelling devices can pull the soft tissue away from the bone and/or cause significant spreading of the incision through a lever action and other movements that help the surgeon insert the cable passer. Cable passers can also increase the risk of arterial strangulation (including the femoral artery) when used, creating unnecessary risk. They can cause excessive tissue damage to patients (for example, stripping of soft tissue away from the bone and/or significant spreading of the incision), leading to additional theatre time and devitalisation of tissue in the wound. A separate tool called a Cerclage Tunnelling Device is used occasionally in tandem to strip away tissue to make a clear path for the cable passer.

Cerclage cables or wires are also used prophylactically to prevent fracture, some are placed separate to a fracture to prevent propagation, and occasionally in revision surgery when repairing an osteotomy (a surgical fracture where a controlled break is created in the bone).

Another problem with standard cable passers is that they do not allow for minimally invasive surgery, and often necessitate the use of a separate instrument called a retractor or self-retainer to keep a large incision spread open to create room for the surgeon to use a clamp and separate cable passer. The use of such retractors also has its problems in that they are an additional instrument and can crowd the wound and block the use of other instruments like the cable passer or clamp. Also, if excessive tissue spreading is performed and maintained for a long period it can damage skin.

Numerous academic sources report the risks of cable passers, highlighting that the deep femoral artery and its perforators are the most commonly damaged, and that during revision total hip arthroplasty it has been reported that the incidence of perforating artery interruption (a major, potentially devastating complication) after femoral wiring is 23.6%.

Furthermore, theatre time is becoming an expensive commodity. The elimination of a complicated, dangerous step in any surgery is a welcome one, but especially when it can save time and improve efficiency.

Attempts have been made to address these problems, such as the cerclage tool described in US2007043377, which comprises two members, each member having a handle, a central part and a J-shaped tube. When the central part of both members is firmly coupled together, both J-shaped tubes conform to a continuous tube through which a wire, cable, band or suture can be fed. The problem with the tool of US2007043377 is that it necessitates a separate bone holding clamp to first align the broken bone pieces. This compromises the placement of the cable in the ideal position. This also creates more work for the user and thus more time spent in surgery.

Chinese Patent Application No. CN2836737Y appears to disclose a bone clamping device for use in bone fracture repair operations, where the jaws of the clamp feature a passageway for a cable. This device has a closed passageway. Therefore, as a clamp it may be useful initially to reduce the bone, but then must be released in order to allow the cable to come in contact with the bone. This would result in loss of reduction.

Chinese Patent Application No. CN103932768A discloses a bone clamp comprising a pair of pivotally connected handles, each providing an arcuate jaw providing a first opening at their proximal end and a second opening distal end, with an open channel extending between the openings, the channel being configured to, and intended for, receipt of a cable or wire. However, with this arrangement, the user must perform an additional step of pulling the cable or wire out of the channel prior to fastening about the bone. This creates more work for the user and thus more time spent in surgery.

This also compromises the placement of the cable in the ideal position.

Cerclage wires (or cables) are typically monofilament wires or multifilament cables. They are used in a variety of orthopaedic applications (see, for example, U.S. Pat. No. 6,045,909). The cables and wires are typically made of stainless steel, titanium, or a cobalt-chromium alloy, having high tensile and fatigue strength. Another problem is that these cables cannot be placed on the optimal fixation location when there is a bone clamp already in the way, as the bone clamp often occupies the optimal location for fixation. The cables have been designed with using a separate cable passer to the bone clamp in mind, creating an additional step that necessitates additional tissue stripping.

It is an object of the present invention to overcome at least one of the above-mentioned problems.

SUMMARY OF THE INVENTION

The invention relates to a bone clamp which can be used to aid in positioning a cable, wire, suture, band or other device around a bone to secure the bone in place so as to prepare the bone for surgery, or for aiding a broken or fractured bone to heal in place.

According to the present invention, there is provided, as set out in the appended claims, a bone clamp (1,200,300) for use in fixation of a fractured bone or prevention of fracture of a bone, the clamp (1,200,300) comprising a pair of handles (2a,2b) joined together at a pivot point (5), the handles (2a,2b) each having an arcuate jaw (4a,4b), the arcuate jaws (4a,4b) comprising a first end (7a,7b) having an opening at a proximal end (12a,12b) of each of the jaws (4a,4b) in communication with a second end (8a,8b) having an opening at a distal end (14a,14b) of the jaw (4a,4b), the first end (7a,7b) and second end (8a,8b) in communication via a channel (6a,6b), in which the channel (6a,6b) is configured to accommodate a cable, a wire, a band, a suture or other device, and characterised in that the channel (6a,6b) is an open channel.

There is also provided a bone clamp (1,200,300) for use in fixation of a fractured bone or prevention of fracture of a bone, the clamp (1,200,300) comprising a pair of handles (2a,2b) joined together at a pivot point (5), the handles (2a,2b) each having an arcuate jaw (4a,4b), the arcuate jaws (4a,4b) each comprising a first end (7a,7b) having an opening at a proximal end (12a,12b) of each of the jaws (4a,4b) in communication with a second end (8a,8b) having an opening at a distal end (14a,14b) of the jaws (4a,4b), the first end (7a,7b) and second end (8a,8b) in communication via a channel (6a,6b), in which the channel (6a,6b) is configured to accommodate a cable, a wire, a band, a suture or other suitable device, and characterised in that the channel (6a,6b) is an open channel which runs through an internal face (10a,10b) of both of the arcuate jaws (4a,4b), respectively.

Preferably, at least one of the first ends (7a,7b) is flared. Ideally, when one of the first ends (7a,7b) is flared, the other end is square, rounded, sloped, flared or rectangular.

Preferably, at least one of the second ends (8a,8b) is flared. Ideally, when one of the second ends (8a,8b) is flared, the other end is square, rounded, sloped, flared or rectangular.

Preferably, the channel (6a,6b) runs through an internal face (10a,10b) of the arcuate jaws (4a,4b). Ideally, at least one of the internal faces (10a,10b) comprises a plurality of ridges (12) running perpendicular to the channel (6a,6b).

Preferably, the arcuate jaws (4a,4b) have an arc measuring between 11.25° and 270°. Ideally, the arcuate jaws (4a,4b) have an arc measuring between 22.5° and 22°.

Preferably, the handles (2a,2b) can slide relative to each other in the same plane at the pivot point (5) where central parts (3a,3b) of the handles (2a,2b) are connected together via a coupling connector (18) and a slot (16).

Preferably, the handles (2a,2b) further comprise a tightening means.

Preferably, the bone clamp (1,200,300) is composed of stainless steel, titanium, carbon steel, graphene, platinum or alloys thereof.

In one aspect, either one or both channels (6a,6b) is inclined at an angle of between about 0.01° to about 45° relative to the central line of the jaw (4a,4b), respectively. Ideally, either one or both channels (6a,6b) is inclined at angle of about 5° relative the central line of the jaw (4a,4b), respectively. In one aspect, only the channel (6a) is inclined at an angle relative to the central line of the jaw (4a). In one aspect, neither one of the channels (6a,6b) is inclined at an angle of between about 0.01° to about 45° relative to the central line of the jaw (4a,4b), respectively.

Preferably, the bone clamp (1,200,300) further comprises a ledge (201) extending outwards from an inside face (202) of the jaw (4b) between the first end (7b) and the central part (3b) of the handle (2b).

Preferably, the bone clamp (1,200,300) further comprises a retractable sleeve (401) extending from the distal end (14b) of one jaw to the distal end (14a) of the other jaw. Ideally, the retractable sleeve (401) is housed within the structure of the jaw (4b). Ideally, the retractable sleeve (401) is integrated along the top of the jaw (4b). Ideally, the retractable sleeve (401) is integrated within the channel (6b) of the jaw (4b). Ideally, the retractable sleeve (401) is accommodated along the surface of (10b) of the channel (6b) of the jaw (4b).

Preferably, the bone clamp (1,200,300) further comprises the central part (3b) of the handle (2b), between the pivot point (5) and the first end (7b), has either a convex or concave surface relative to the central plane of the channel (6b).

Preferably, the bone clamp (1,200,300) further comprises a shelf (460) extending outward from the external wall (19a) of the jaw (4a).

There is also provided, as set out in the appended claims, a cable (100) for use with the bone clamp (1,200,300) described above, the cable (100) comprising a body (101) and a tip (102), characterised in that the tip (102) is stiffened and has an uncurved portion (102b) between the cable body (101) and the tip (102).

In one aspect, the tip (102) of the cable (100) further comprises a bevelled end point (102a). Preferably, the tip (102) is curved between the uncurved portion (102b) and the bevelled end point (102a). In one aspect, the bevelled end point (102a) of the tip (102) has an arc that matches that of an arc of the arcuate jaws (4a,4b) of the clamp (1,200,300) described above. In one aspect, the bevelled end point (102a) further comprises edges (202a,202b) and sides (202c, 202d) that are adapted to match the cross-sectional shape of the openings 7b,8a of the bone clamp (1,200,300) described above.

There is also provided a cable (100) for use with the bone clamp (1,200,300) described above, the cable (100) comprising a body (101) and a tip (102), characterised in that the tip (102) is stiffened and has an uncurved portion (102b) between the cable body (101) and the tip (102), wherein the tip (102) is curved between the uncurved portion (102b) and the bevelled end point (102a).

In one aspect, the bevelled end point (102a) of the tip (102) has an arc that matches that of an arc of the arcuate jaws (4a,4b) of the clamp (1,200,300) described above. In one aspect, the bevelled end point (102a) further comprises edges (202a,202b) and sides (202c,202d) that are adapted to match the cross-sectional shape of the openings 7b,8a of the bone clamp (1,200,300) described above.

There is also provided a cable (100) for use with the bone clamp (1,200,300) described above, the cable (100) comprising a body (101) and a tip (102), characterised in that the tip (102) is stiffened and has a bevelled end point (102a) and an uncurved portion (102b) between the cable body (101) and the tip (102), wherein the tip (102) is curved between the uncurved portion (102b) and the bevelled end point (102a) and wherein the tip (102) has a cross-sectional shape adapted to engage with the channel (6a,6b) of the bone clamp (1,200,300) described above having a similar cross-sectional shape.

In one aspect, the bevelled end point (102a) further comprises edges (202a,202b) and sides (202c,202d) that are adapted to match the cross-sectional shape of the openings 7b,8a of the bone clamp (1,200,300) described above.

In one aspect, the cross-sectional shape is four-sided or substantially circular. Preferably, four-sided cross-sectional shape has rounded edges.

Preferably, the curved portion between the uncurved portion (102b) and the bevelled end point (102a) of the tip (102) has an arc that matches that of an arc of the arcuate jaws (4a,4b) of the clamp (1,200,300) described above.

In one aspect, the tip (102) has an arc measuring between 11.25° and 270°. Ideally, the tip (102) has an arc measuring between 22.5° and 225°.

Preferably, the tip (102) is fixed to the body (101) of the cable (100) by welding, gluing, snap-fit, threaded or male to female connections.

Preferably, the cable (100) is made from medical grade materials such as stainless steel, titanium, cobalt-chromium-molybdenum alloys (vitallium®), carbon steel, graphene, platinum, biocompatible polymers, and alloys thereof, or combinations thereof.

Preferably, the tip (102) has a cross-sectional shape selected from a square, a rectangle, a triangle, an ellipse, a pentagon, a hexagon, a heptagon, an octagon, a star shape, substantially flat, oval, rounded edges, or combinations thereof.

There is also provided a kit for use in internal fixation of a fractured bone or prevention of a fracture of a bone, the kit comprising the bone clamp (1,200,300) and the cable (100) described above.

There is also provided a method for fixing a fracture or preventing fracture of a bone, the method comprising affixing the bone clamp (1,200,300) described herein to a bone to reduce a bone fracture or prevent a fracture; passing the cable (100) described herein through the channels (6a,6b) of the bone clamp (1,200,300); applying a crimp to the cable (100); tightening the cable (100) by a cable tightening means; and crimping the crimp to fasten the cable (100) in place.

Preferably, the bone clamp (1,200,300) is removed once the cable is tightened and before the crimp is crimped or is removed after the crimp is crimped.

Definitions

In the specification, the term "cerclage wire", "wire" or "cable" should be understood to mean any type of ortho-paedic fixation/stabilisation material (such as a cable, a wire, a suture, a band, or other suitable flexible material) placed to approximate and hold in place fractured bone fragments or placed to prevent fracture of bones. The terms may be used interchangeably.

In the specification, the term "bone clamp" should be understood to mean an orthopaedic instrument for (a) reducing/realigning a broken bone and (b) clamping a fracture in place and (c) passing a (orthopaedic) wire, a (orthopaedic) cable, a band, a suture or a suitable flexible material through the bone clamp and around the bone for fixation of a fracture.

In the specification, the term "long bone fracture" should be understood to mean fractures to a long bone, such as, a femur, a tibia, a fibula, a humerus, a radius and an ulna. It may also refer to a clavicle, a metacarpal, and a metatarsal.

In the specification, the term "long oblique bone fracture" should be understood to mean a fracture that has a long portion at an acute angle to the long axis of the bone. This results in a long fracture.

In the specification, the term "short oblique bone fracture" should be understood to mean a fracture that has a less oblique/more obtuse angle to the long axis of the bone. This results in a shorter fracture.

In the specification, the term "pincer-like" should be understood to mean a tool having two handles and two grasping jaws working on a pivot and used for gripping a target of interest, such as a bone.

In the specification, the term "arcuate" should be understood to mean having a curved shape.

In the specification, the term "flared" should be understood to mean a shape which is wider at the top than at the base, that is, one end is wider than the other end.

In the specification, the term "stiffened" or "stiffness" should be understood to mean that the tip of the cable of the invention has a stiffness (a Young's Modulus value) that is up to 1.1, 1.2, 1.3, 1.4, 1.5, 1.6, 1.7, 1.8, 1.9, 2, 2.5, 3, 3.5, 4, 4.5, 5, 5.5, 6, 6.5, 7, 7.5, 8, 8.5, 9, 9.5, 10, 15, 20, 25, 30, 35, 40, 45 or 50-times the Young's Modulus (measure of the stiffness of a solid body) value of the body of the cable. The tip of the cable of the invention may also have a stiffness based, in part, on the stiffness of the cable and the material that the cable is made from. Further, the stiffness of the tip may be increased or decreased by changing the diameter or cross-sectional area of the tip. Note that the stiffened tip might be arranged such that its properties change along its length, to make it selectively more or less bendable in certain zones, for example. This might be accomplished by, for example, heat treating, crimping, placing holes in, taper-ing, flattening, or notching the or near the tip so that a tighter bend can be formed.

In the specification, the term "tip", when used in relation to the tip of the cable of the invention, should be understood to mean the leading end of the substantially circular or tubular cable that is passed through the bone clamp first has a tip that has a cross-sectional shape selected from a square, a rectangle, a triangle, an ellipse, a pentagon, a hexagon, a heptagon, an octagon, a star shape, substantially flat (with rounded edges), oval, and the like. Preferably, the tip is non-stranded.

The optimal arc length of the tip of the cable is between about 5 mm and 100 mm when using a (typical femur mid-shaft) diameter of curvature of 20, 21, 22, 23, 24, 25, 26, 27, 28, 29 or 30 mm. The optimal arc length will probably be between about 10 mm and about 70 mm; preferably between about 15 mm and 65 mm; ideally between about 20 mm and 55 mm; or more specifically, about 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 v, 40 mm, 41 mm, 42 mm, 43 mm, 44 mm, 45 mm, 46 mm, 47 mm, 48 mm, 49 mm, 50 mm, 51 mm, 52 mm, 53 mm, 54, and 55 mm.

The plane of the channel 6a can be off-centre of the surface of the jaw 4a by between about 0.01°, 0.05°, 0.1°, 0.5°, 1°, 1.5°, 2°, 2.5°, 3°, 3.5°, 4°, 4.5°, 5°, 5.5°, 6°, 6.5°, 7°, 7.5°, 8°, 8.5°, 9°, 9.5°, 10°, 10.5°, 11°, 11.15°, 12°, 12.5°, 13°, 13.5°, 14°, 14.5°, 15°, 15.5°, 16°, 16.5°, 17°, 17.5°, 18°, 18.5°, 19°, 19.5°, 20°, 20.5°, 20°, 20.5°, 30°, 30.5°, 40° or about 45° relative to the central line of the jaw 6a. The plane of the channel 6b can also be off-centre to the surface of the jaw 4b by between about 0.01°, 0.05 °, 0.1°, 0.5°, 1°, 1.5°, 2°, 2.5°, 3°, 3.5°, 4°, 4.5°, 5°, 5.5°, 6°, 6.5°, 7°, 7.5°, 8°, 8.5°, 9°, 9.5°, 10°, 10.5°, 11°, 11.15°, 12°, 12.5°, 13°, 13.5°, 14°, 14.5°, 15°, 15.5°, 16°, 16.5°, 17°, 17.5°, 18°, 18.5°, 19°, 19.5°, 20°, 20.5°, 20°, 20.5°, 30°, 30.5°, 40° or about 45° relative to the central line of the jaw 6b.

The curvature (inner) diameter of the tip of the cable (that is, the diameter measured at the inner surface of the cable relative to the bone) is substantially equal to or no more than 50% smaller than the bone diameter being operated on. Preferably, the curvature (inner) diameter of the tip of the cable is between 1-25% less than the bone diameter being operated on. In one aspect, the curvature (inner) diameter of the tip of the cable is slightly larger, that is, no more than 10% larger, than the diameter of the bone being clamped/ operated on. The inner diameter of the curvature of the tip of the cable is the measurement from the inner surface of the cable tip.

In the specification, the term "substantially equal to" should be understood to mean to be within plus or minus 2% of, plus or minus 1% of, or exactly equal to, the diameter of the bone being operated on.

In the specification, the term "ridges(s)", when used in relation to the jaw(s) of the bone clamp, should be understood to mean a corrugated shape, with either sharp or rounded peaks and troughs, or a combination thereof.

In the specification, the term "biocompatible polymers" should be understood to mean synthetic or natural polymers which do not react with any tissue or bodily fluid in the body, and are non-carcinogenic, non-toxic, non-allergenic, non-inflammatory and blood compatible. Examples of suitable biocompatible polymers are polyvinylchloride (PVC), polytetrafluoroethylene (PTFE), polyethersulfone (PES), polysulfone (PS), polyethylene.

In the specification, the term "composite materials" should be understood to mean biocompatible composite materials which do not react with any tissue or bodily fluid in the body, and are non-carcinogenic, non-toxic, non-allergenic, non-inflammatory and blood compatible. Examples of suitable composite materials are platinum with nylon, polyetheretherketone (PEEK) polymer reinforced with continuous carbon fibre, polyetheretherketone (PEEK) polymer reinforced with continuous carbon fibre combined with hydroxyapatite, carbon nanotube (CNT) polymer composites, Kevlar®, ceramic matrix composites, and the like.

In the specification, the term "tightening the cable" should be understood to mean putting tension on or tensioning the cable.

BRIEF DESCRIPTION OF THE DRAWINGS

The invention will be more clearly understood from the following description of an embodiment thereof, given by way of example only, with reference to the accompanying drawings, in which:

FIG. 7 illustrates a perspective view of the cable of the present invention.

DETAILED DESCRIPTION OF THE DRAWINGS

Materials

The bone clamp of the invention is typically constructed from medical grade materials such as stainless steel, titanium, carbon steel, graphene, platinum, biocompatible polymers, ceramic, composite materials, and alloys thereof.

The cable of the invention is typically made from medical grade materials such as stainless steel, titanium, vitallium® (an alloy comprising 65% cobalt, 30% chromium, 5% molybdenum), carbon steel, graphene, platinum, biocompatible polymers, and alloys thereof.

Methods of Manufacture of the Cable

The cable is typically manufactured by the standard methods known to the skilled person (for example, see the methods disclosed in European Patent Application No. 0916315). The tip at the end of the cable is stiffer than that of the cable body. The tip is attached to the cable by methods known to the skilled person. For example, the stiffened tip is attached to the cable body by welding, threading, gluing, a snap-fit connection, a male-female connection, and the like.

Method of Use

The traditional method using a clamp and cable passer generally involved the following steps:

1. Skin and soft tissue incised to gain access to the fracture.
2. Optional: Self-retainer (retractor) inserted to allow further exposure and insertion of further instruments
3. Fracture reduced using a clamp.
4. Soft tissue stripped to allow passage of cable passer
5. Cable passer used in separate position to clamp, resulting in more soft tissue stripping.
6. Cable passed through cable passer.
7. Cable passer removed.
8. Crimp applied to cable.
9. Cable tightener applied to cable and cable tightened.
10. Crimp "crimped" to fasten cable in place.
11. Clamp removed.

The method using the bone clamp of the claimed invention and described herein is as follows:

1. Skin and soft tissue incised to gain access to the fracture.
2. Optional: Self retainer inserted to allow further exposure.
3. Fracture reduced using a clamp.
4. Cable passed through clamp.
5. Crimp applied to cable.
6. Cable tightener applied to cable and cable tightened.
7. Crimp "crimped" to fasten cable in place.
8. Clamp removed.

By comparing both methods above, it can be seen that there are less steps and less instruments used in the claimed invention.

Description

The present invention provides a bone clamp and a cable for use therewith. The bone clamp is configured such that a separate bone clamp and/or cable passer is not required, thus reducing the risk of rupturing an artery and stripping away tissue from the bone during use.

Figure 1A:
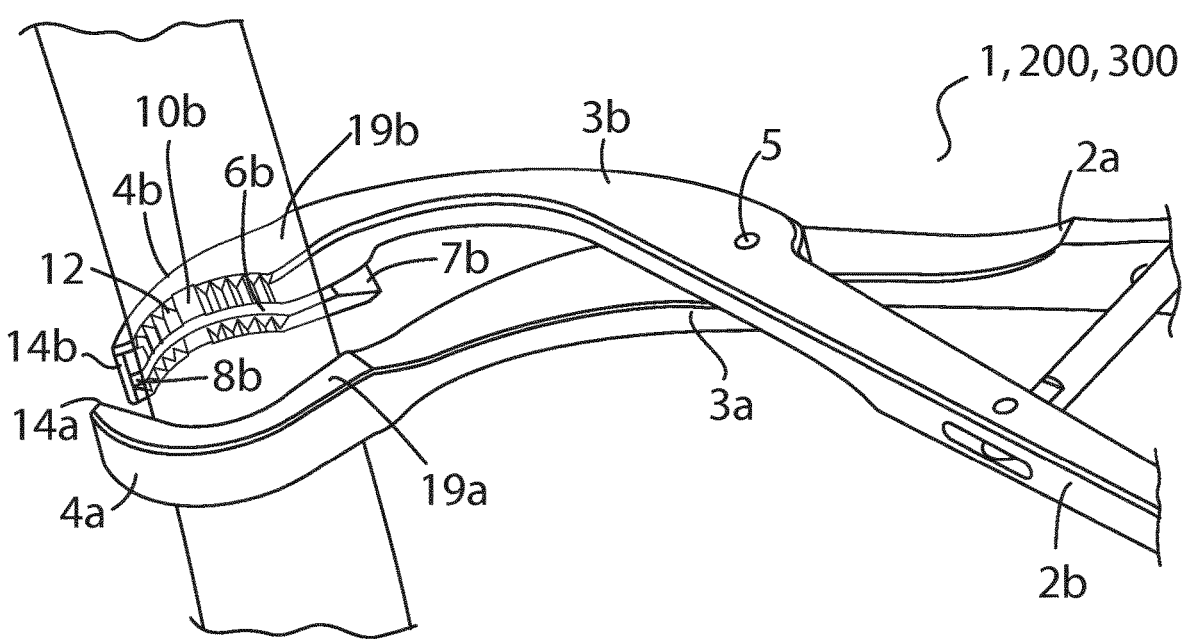
FIG. 1A illustrates a perspective view of the bone clamp of the present invention grasping a bone and FIG. 1B illustrates a further perspective view of the jaws of the bone clamp of the present invention grasping a bone.
Figure 1B:
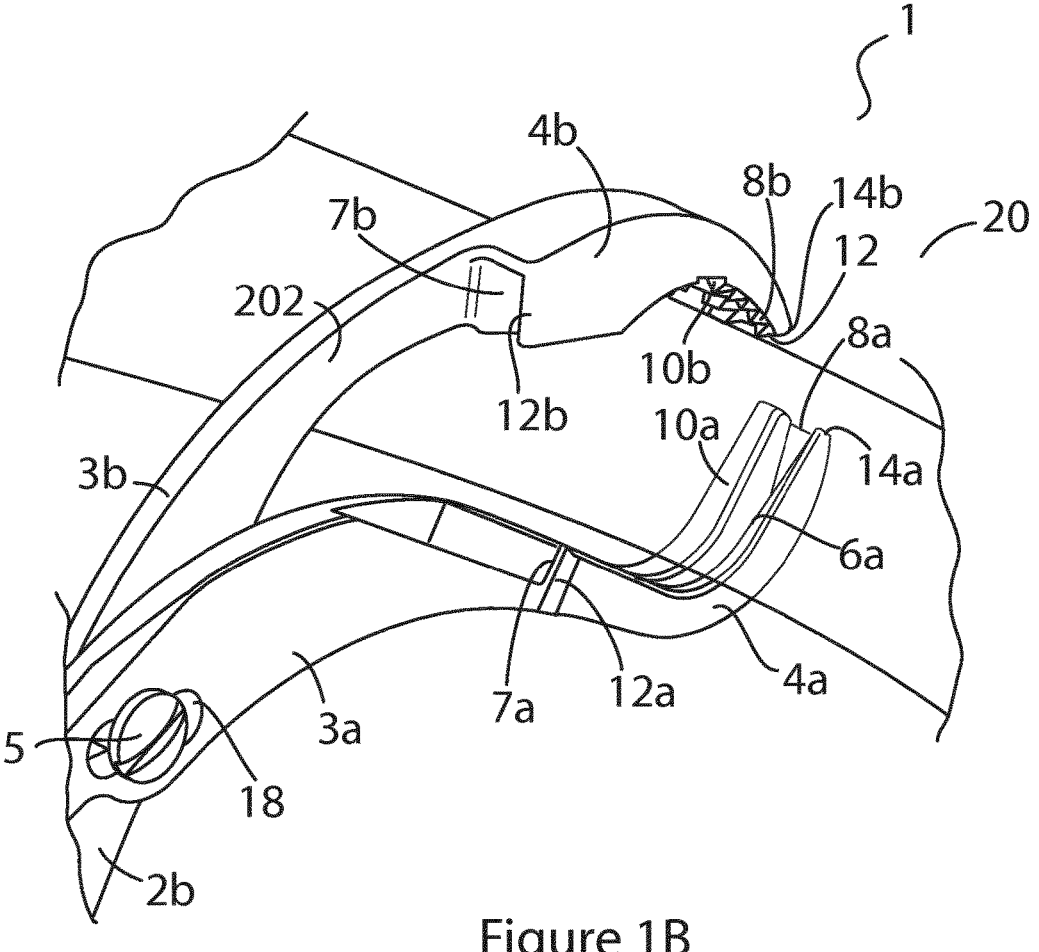

Referring now to the figures, wherein FIG. 1A-B illustrates a general embodiment of a bone clamp of the present invention. Specifically, FIG. 1A illustrates a perspective view of a bone clamp of the present invention and is generally referred to by reference numeral 1. The bone clamp 1 of the illustrated embodiment comprises a pair of handles 2a,2b, each handle 2a,2b having a central part 3a,3b, respectively, and a jaw 4a,4b, respectively. The central parts 3a,3b are secured together at a pivot point 5 to form a pincer-like head arrangement 20. The pivot point 5 is where the jaws 4a,4b move in the same plane. The jaws 4a,4b comprise a channel 6a,6b, respectively, the channels 6a,6b having a first open end 7a,7b at a proximal end 12a,12b of the jaw 4a,4b, respectively, and a second open end 8a,8b at a distal end 14a,14b of the jaws 4a,4b, respectively. The channels 6a,6b are configured to accommodate a cable, tie or suture. This combination of features can collectively be called the head 20 of the bone clamp 1.

External walls 19a,19b of the jaws 4a,4b can be tapered inwards towards open ends 8a,8b, respectively. Essentially, this is to provide a slim profile for the head 20 to minimize tissue disturbance and minimizes invasiveness when in use. Such a taper reduces cross-sectional area of the head 20 by up to 60%.

Figure 1C:
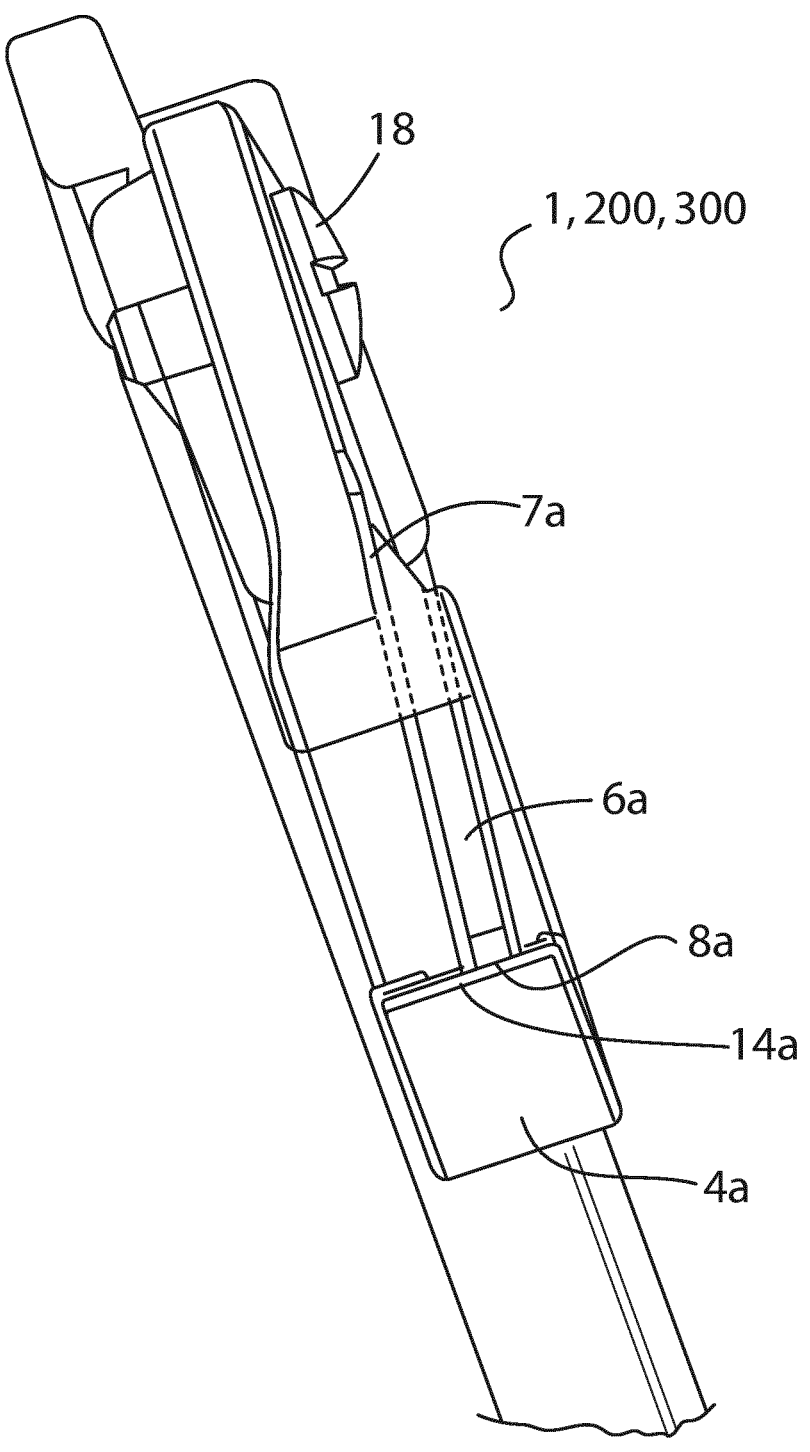
FIG. 1C illustrates a plan view of one of the jaws of the bone clamp of the present invention where the channel of one of the jaws is not central to the plane of the channel of the other jaw.

Typically, the channel 6a is in the same plane as the channel 6b, that is, it is parallel to the sides of the jaw 4a. The plane of the channel 6b is typically central in the jaw 4b. In one embodiment, as shown in FIG. 1C, the channel 6a is not in the same plane as the channel 6b, that is, it is not parallel to the sides of the jaw 4a. The plane of the channel 6a is shown here to be off-centre of the surface of the jaw 4a and guides a cable away from the centre of the head 20 of the bone clamp 1 as the cable exits. The channel 6a in this embodiment is between 0.01° to 45° from the central line of the jaw 4a. The advantage to this is that it reduces the risk of a tip of the cable getting snagged on the handle 2b or the other parts of the bone clamp 1. It also reduces the risk of the rear of the cable (which is entering channel 6a) obstructing the exit of the tip of the cable. It makes it easier for the user to grab/take hold of the receiving end of the cable (the tip). It should be also be noted that the plane of the channel 6b can be off-centre of the surface of the jaw 4b and guides a cable towards the centre of the head 20 of the bone clamp 1 as the cable enters the clamp. This arrangement can be present when the channel 6a is off-centre, as descried, or when the channel 6a is not, thus leaving only channel 6b being off-centre. The clamp 1 can also be arranged where the channels 6a,6b are not inclined relative to the jaw 4a,4b, respectively.

Figure 2:
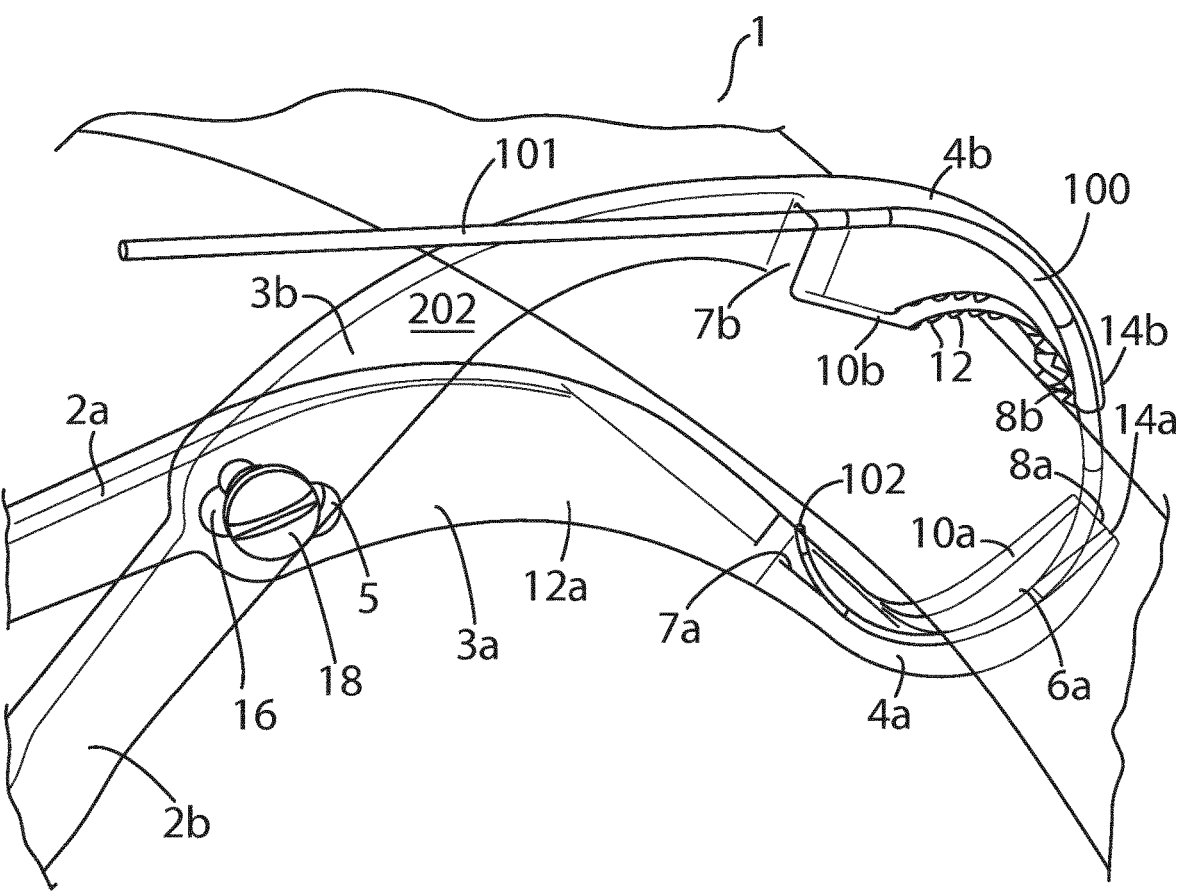
FIG. 2 illustrates a cable passing through the jaws of the clamp of FIG. 1.

The handles 2a,2b are secured at the pivot point 5 by a coupling connector 18 (see also FIG. 2). The coupling connector 18 on handle 2b engages with a slot 16 on handle 2a (it should be noted that the connector 18 and slot 16 can also be reversed and can be on handle 2a and 2b, respectively). The connector 18 is accommodated within the slot 16 such that the connector 18 is free to move within the confines of the slot 16. This allows the user to move the handles 2a,2b relative to each other in the same plane and into a preferred position to permit the jaws 4a,4b to securely hold on to a target bone. Once the jaws 4a,4b of the handles 2a,2b are in the preferred position, the user tightens a tightening means on the handles 2a,2b (not shown) to keep the handles 2a,2b from moving relative to one another. In other words, the handles 2a,2b are fixed in place.

Turning now to FIG. 2, a more detailed view of the jaws 4a,4b of the bone clamp 1 is illustrated. As shown, the jaw 4b further comprises an internal face 10b, which further comprises a series of ridges 12 traversing the width of the jaw 4b (see FIG. 1A and 1B also). The ridges 12 aid in gripping the bone to be treated when the bone clamp 1 is in use. The jaw 4b typically has an arcuate shape, which also aids in gripping the bone when in use. The opening 8b at the distal end 14b of the channel 6b is generally parallel with the sides of the channel 6b and has a substantially rectangular shape in cross-section. However, the shape of the opening 8b can also be rounded, squared-off, sloped, flared, triangular, have filleted corners, funnel-like, conical, hemi-spherical, and the like. The advantage of the opening 8b having parallel sides is that it controls and/or restrains the rotation/toggle of the tip of a cable having parallel sides as it leaves the channel 6b to enter channel 6a.

The jaw 4a further comprises an internal face 10a, which faces the internal face 10b but which may or may not have a series of ridges. The opening 8a at the distal end 14a of the channel 6a is flared, which means that the opening 8a gradually becomes wider at the distal end 14a of the channel 6a as the channel moves from proximal end of the jaw 4a to the distal end of the jaw 4a. The flared opening 8a provides the advantage of creating a larger receiving and guidance zone for the tip of a cable as the cable passes from one jaw 4a to the other jaw 4b (or vice versa), thus helping to correct any "toggle" or lateral movement of the cable by guiding it back into the correct plane of channel 6a. The opening 8a is flared both in the "left/right" direction and vertically, creating a funnel effect. The funnel effect of the opening 8a guides the cable towards the centre of the channel 6a to provide a "lead-in" for the cable to aid correct positioning of the cable within the head 20 of the bone clamp 1, and subsequently around the shaft of the bone of interest.

The opening 7b at the proximal end 12b of the channel 6b is flared, which means that the opening 7b is wider at the proximal end 12b of the channel 6b as the channel moves from distal end 14b of the jaw 4b to the proximal end 12b of the jaw 4b. The flared opening 7b provides the advantage of creating a larger receiving and guidance zone for the tip of a cable as the cable enters into the jaw 4b and the channel 6b, thus helping to correct any "toggle" or lateral movement of the cable by guiding it back into the correct plane of channel 6b. The opening 7b is flared both in the "left/right" direction and vertically, creating a funnel effect. The funnel effect of the opening 7b guides the cable towards the centre of the channel 6b to provide a "lead-in" for the cable to aid correct positioning of the cable within the head 20 of the bone clamp 1, and subsequently around the shaft of the bone of interest.

It should also be understood that the openings and ends 7a, 14a and 8b can also be flared, thus providing the same advantages as set out above for openings 8a,7b and ends 12b,14b. This would also be advantageous if one wishes to use the clamp 1 by first inserting a cable (or another suitable tie) through the opening 7a first rather than through the opening 7b first.

The channels 6a,6b are open along their length, that is, the channels 6a,6b are exposed and are not covered by the surface of the internal faces 10a,10b. The channels 6a,6b typically have unetched surfaces and do not have the same ridges 12 that optionally traverse the internal surface 10a or 10b (or both) of jaws 4a or 4b (or both). The advantage of having open channels 6a,6b is that a cable can be affixed to a clamped bone without having to remove the bone clamp 1. Thus, the requirement for using a separate cable passer in conjunction with a bone clamp is moot.

Typically, the arc length of the jaws 4a,4b is such that when the jaws 4a,4b are engaged on a bone, their distal ends 14a,14b never touch. One of the advantages of this is that it allows tightening of the bone clamp of the invention around the bone to be regulated through the activation of the tightening means, freeing up the user's hands to use other tools, or to pick up the cable described herein with another hand. It also allows the clamp to be used on a variety of bone diameters.

Figures 3, 4:
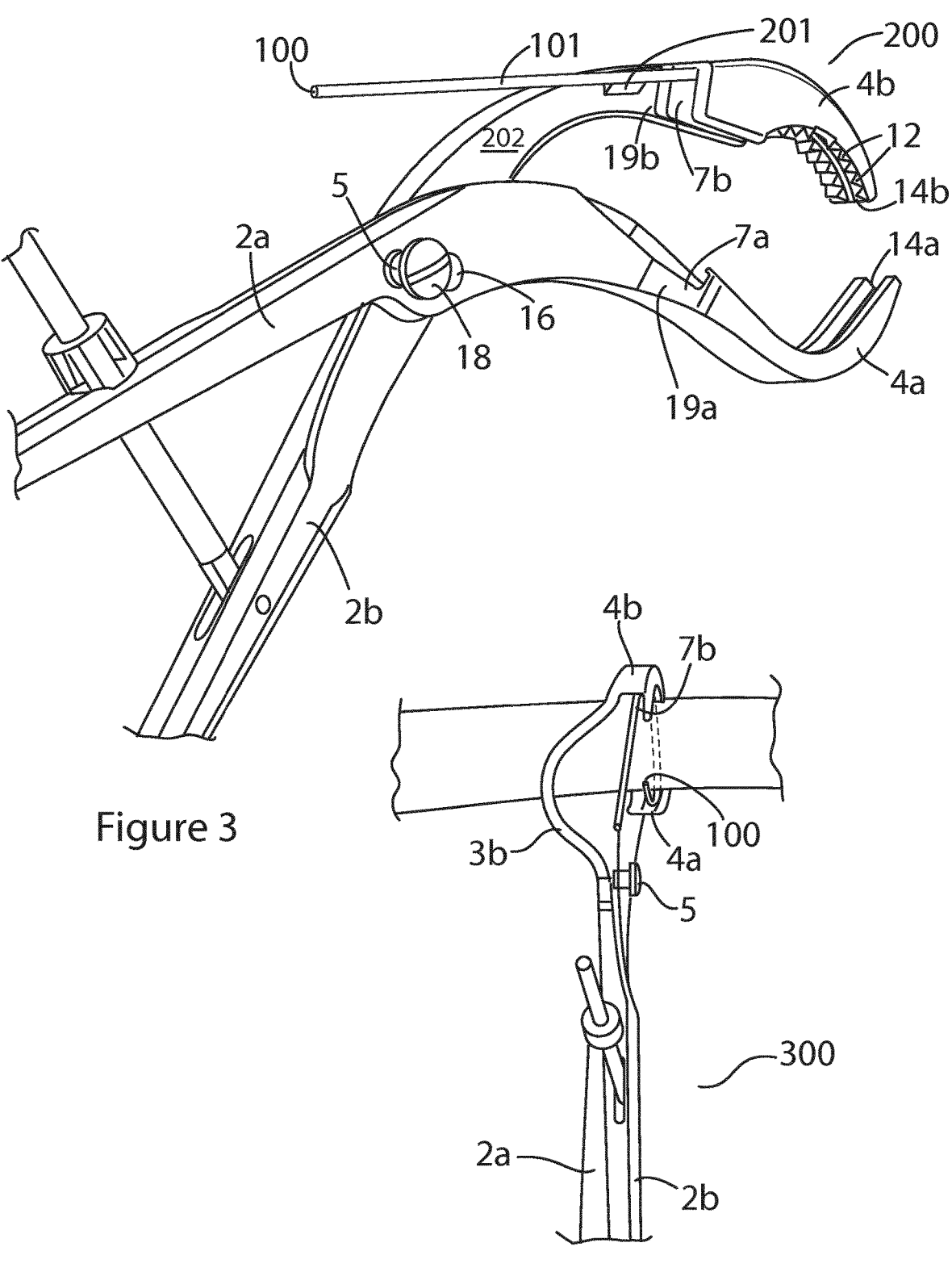
FIG. 3 illustrates a further embodiment of the bone clamp of the invention.
FIG. 4 illustrates a further embodiment of the bone clamp of the invention.

Referring to FIG. 3, there is illustrated a further embodiment of the bone clamp of the invention in which parts or steps described with reference to the previous embodiment are assigned the same numerals. In the embodiment, a bone clamp 200 further comprises a ledge 201 extending outwards from an inside face 202 of the jaw 4b between the first open end 7b and the central part 3b of the handle 2b (that is, the area near the entrance that the cable enters into the channel 6b). The ledge 201 is configured to accept and guide the entry plane of the cable when the cable is being inserted into the open end 7b of the bone clamp 200. The ledge 201 prevents the cable from going in "too low" at the first open end 7b, which would cause the distal end of the tip of the cable to potentially travel off too high and away from the bone of interest. The ledge 201 also ensures that the distal end of the cable enters at the correct angle.

Turning now to FIG. 4, there is illustrated a further embodiment of the bone clamp of the invention in which parts or steps described with reference to the previous embodiments are assigned the same numerals. A bone clamp 300 of the illustrated embodiment comprises the pair of handles 2a,2b, each handle 2a,2b having the central part 3a,3b, respectively, and the jaw 4a,4b, respectively. The central parts 3a,3b are secured together at the pivot point 5 to form a pincer-like head arrangement. The jaw 4b is shown with the first open end 7b at a proximal end 12b of the jaw 4b. In the embodiment, the bone clamp 300 comprises the central part 3b, which can have either a concave or a convex surface relative to the central plane of the channel 6b. The convex or concave surface of the central part 3b creates more space for the user when using crimpers or other tools while the clamp 300 is still in place.

Figure 5A:
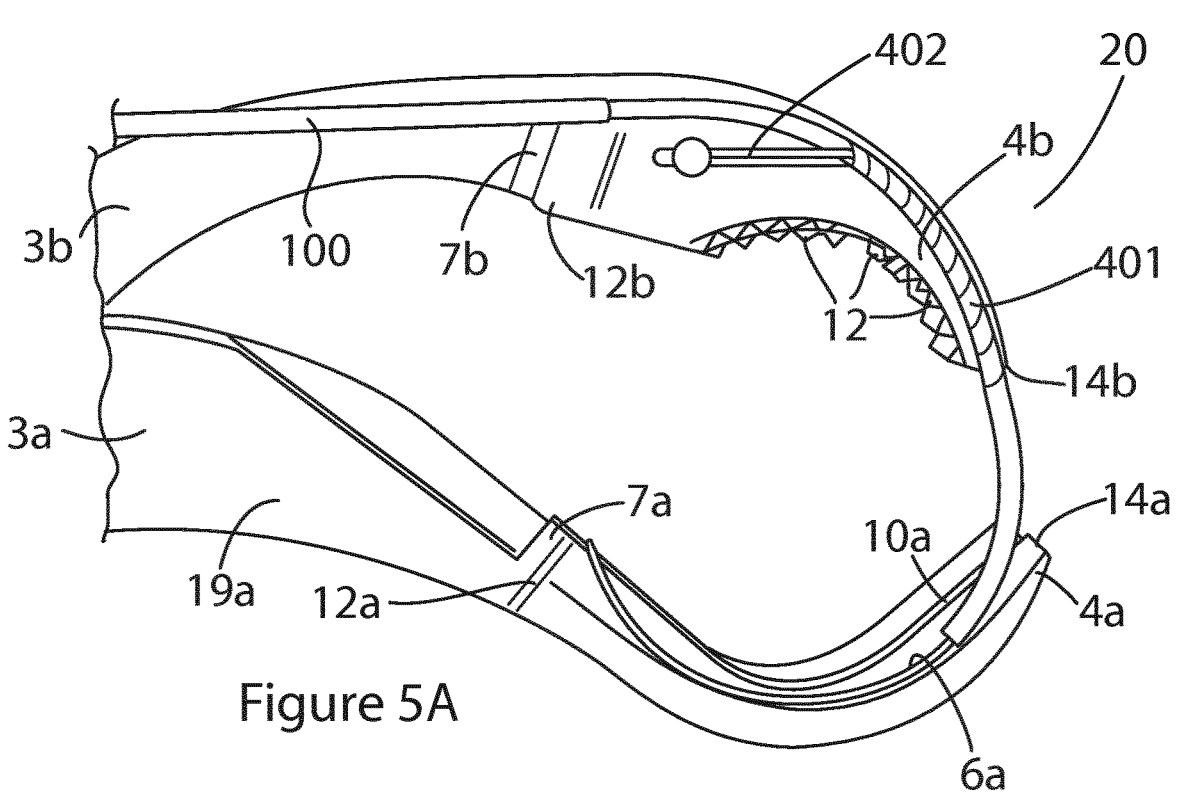
FIG. 5A and FIG. 5B illustrate side views of a further embodiment of the bone clamp of the invention.
Figure 5B:
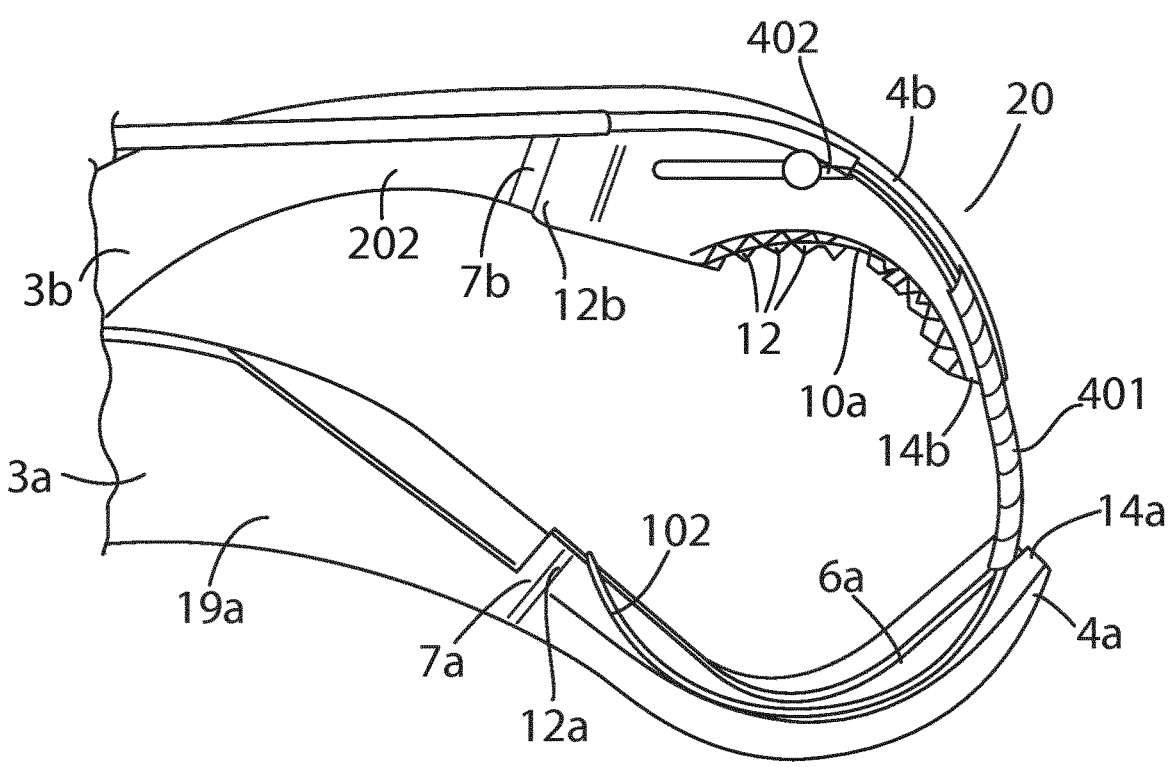

In one embodiment, one or both of the jaws 4a,4b of the bone clamp 1,200,300 of the present invention further comprise a retractable sleeve 401. The retractable sleeve 401 extends from the distal end 14b of one jaw 4b towards the distal end 14a of the other jaw after the bone clamp 1,200,300 is set on a bone of interest. This guarantees a guided path for a cable around the bone of interest as it passes from one jaw to another. This embodiment is illustrated in FIG. 5A and FIG. 5B, in which parts or steps described with reference to the previous embodiments are assigned the same numerals. The sleeve 401 is typically an open channel housed within jaw 4b. The sleeve 401 may also form part of the structure of the jaw, such as the outer surface of the jaw structure, such as on the top surface of the jaw. The sleeve 401 may also be housed within the channel 6a,6b, respectively.

The sleeve 401 is designed to be a continuation of the channel 6b and typically has a radius of curvature that matches the bone it is encircling. After the bone is clamped and the tightening means activated, a lever 402 is activated which acts on the sleeve 401 to exit the distal end 14b of the jaw 4b and communicate with the distal end 14a of the jaw 4a. The communication with the distal end 14a bridges the gap, in part or in full, between the jaws 4a,4b in a typical blind spot for the user, and helps guarantee safe passage of the cable tip around the bone. It should be noted that the sleeve 401 described above may also be housed in jaw 4a and communicate with the distal end of jaw 4b.

Figure 6:
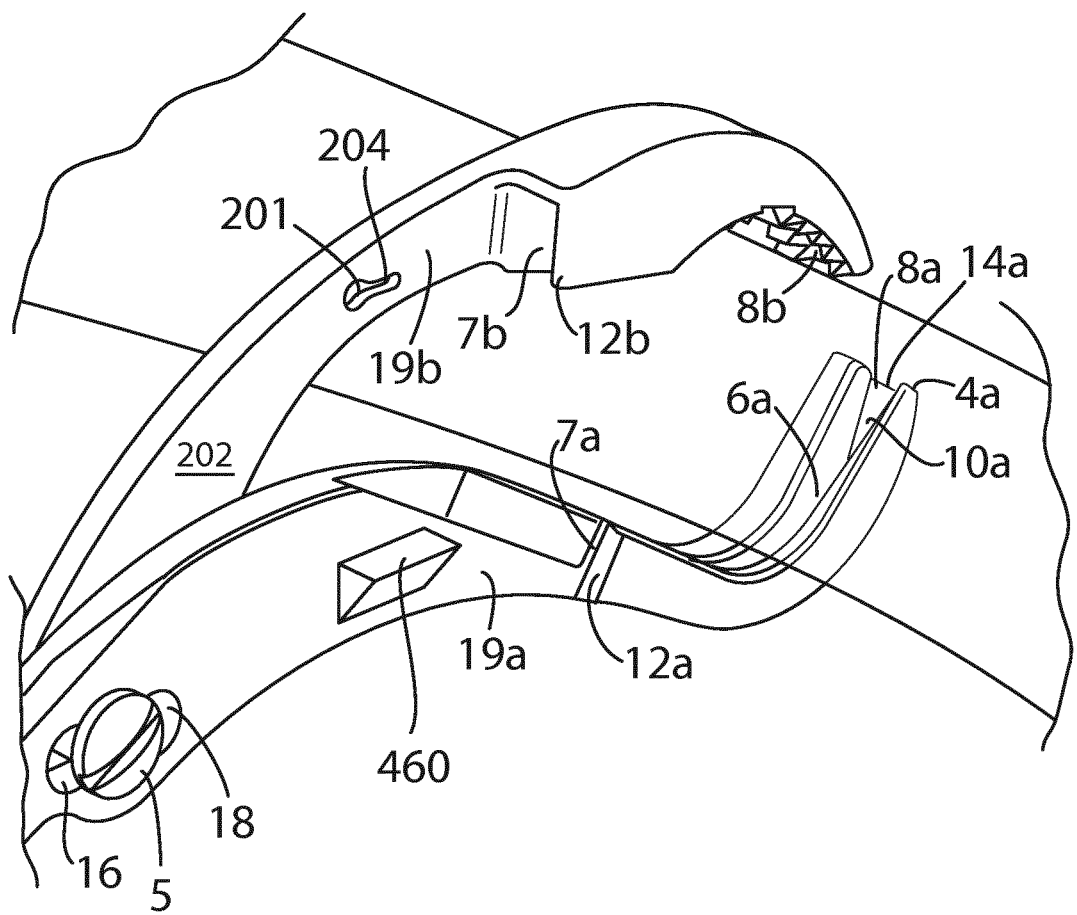
FIG. 6 illustrates a further embodiment of the bone clamp of the invention.

Turning now to FIG. 6, there is illustrated a further embodiment of the bone clamp of the invention in which parts or steps described with reference to the previous embodiments are assigned the same numerals. The bone clamp 1,200,300 of the illustrated embodiment shows the central part 3a,3b and the jaw 4a,4b. The central parts 3a,3b are secured together at the pivot point 5 to form a pincer-like head arrangement 20. The pivot point 5 is where the jaws 4a,4b move in the same plane. The jaws 4a,4b comprise the channel 6a,6b, respectively, the channels 6a,6b having the first open end 7a,7b at the proximal end 12a,12b of the jaw 4a,4b, respectively, and the second open end 8a,8b at a distal end 14a,14b of the jaws 4a,4b, respectively. The channels 6a,6b are configured to accommodate the cable, tie or suture.

FIG. 6 shows the jaw 4b with the ledge 201 that may be used to help guide other tools, such as tensioning and crimping tools, into the optimal position. The ledge 201 extends outwards from the inside face 202 of the jaw 4b, as described above in FIG. 3. The ledge 201 typically has a shallow groove 204 that is shaped to accommodate a tensioner or cable during use. During minimally invasive techniques, the surgeon may not have direct vision of the clamp and will be performing the initial reduction with the clamp via feel of the fracture and X-ray imaging intra-operatively. As a consequence, after inserting the cable and crimp, the tensioner and crimper must be applied, all through a small incision. The use of the ledge 201 is a means to ensure that the tensioner applies the tension to the crimp directly, and that the crimper is applied correctly to the crimp (without direct vision).

Alternatively, or in tandem, the jaw 4a further comprises a shelf 460 configured to accommodate a crimper. The shelf 460 extends outwards from the external wall 19a of the jaw 4a, proximal the first open end 7a.

Figures 7, 7A, 7B:
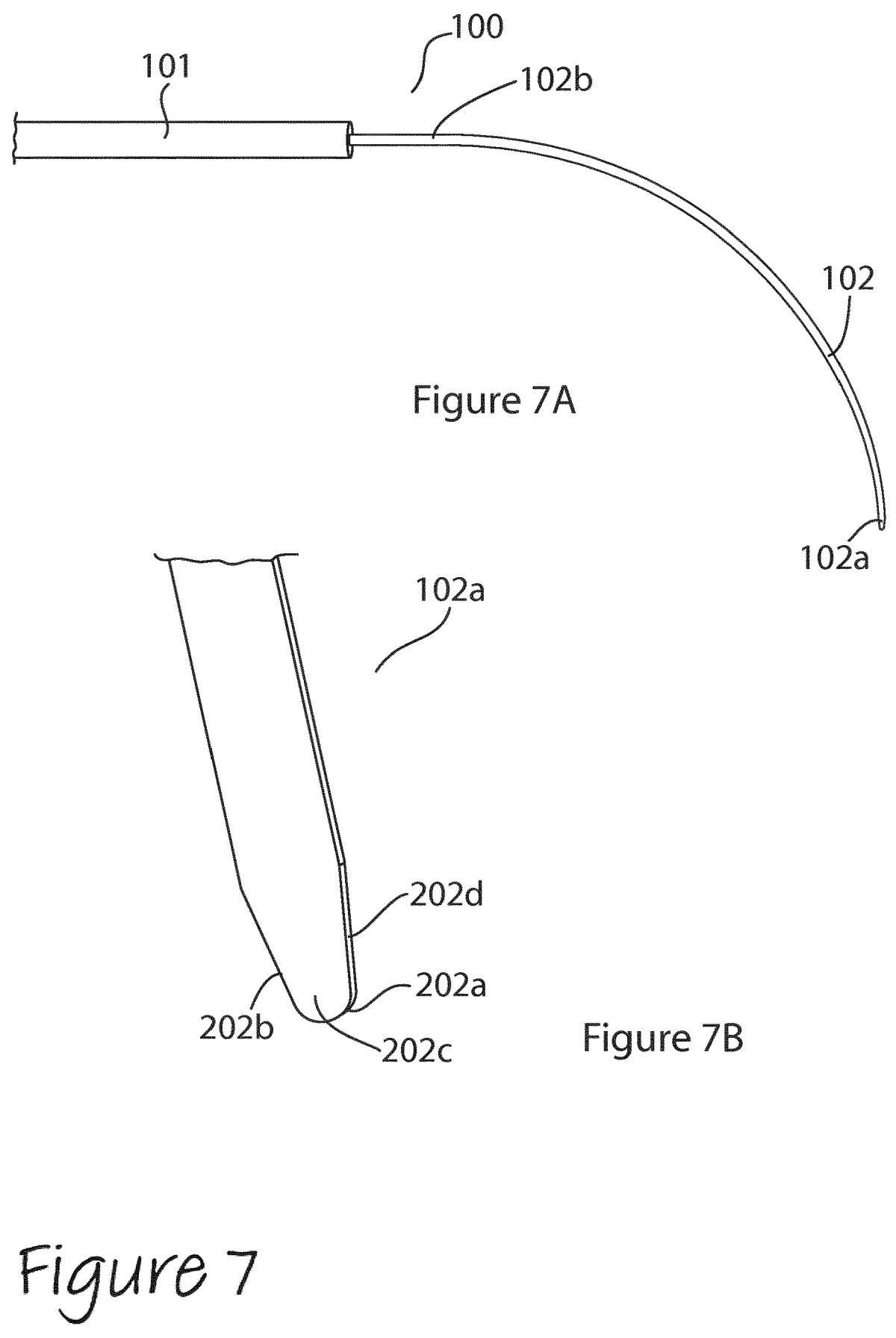

Turning now to FIG. 7A and 7B, which illustrates a general embodiment of a cable of the present invention. Specifically, FIG. 7A illustrates a perspective view of a cable of the present invention and is generally referred to by reference numeral 100. The cable 100 is also shown in FIG. 2, the cable 100 comprising a body 101 and a stiffened tip 102. The stiffened tip 102 can be either continuous or attached at one end of the body 101 of the cable 100. Optionally, the tip 102 can be at both ends of the body 101. The cable body may have a band weld finish to allow for better welding or connection to a stiffened tip with a different cross-sectional area. This band weld finish may be tapered or shaped in such a way to provide a better matching mating surface shape and area to connect/weld/glue with a stiffened tip. This band weld also secures a plurality of individual strands into one non-braided, solid surface to be connected to. The tip 102 can be attached to the cable body 101 by welding, gluing or other methods known to the skilled person. The tip 102 is curved and typically has a flattened or thinner profile in relation to the circular (or non-circular) profile of the cable body 101. However, the shape of the tip 102 in cross-section can be in the form of a square, a rectangle, a triangle, an ellipse, a pentagon, a hexagon, a heptagon, an octagon, a star shape, a substantially flat shape, an oval, and the like, with the cross-sectional typically having rounded edges. The shape of the curved tip 102 is configured to be accommodated within the channel 6a,6b of the bone clamp 1, which act as a natural guide for the cable 100. In other words, the cross-sectional shape along the tip 102 (but not the end) matches the cross-sectional shape of the channel 6a,6b. Further, the curvature of the tip 102 is to mimic both the radius of the bone it is encircling, but also the curvature of the channel 6a,6b and jaws 4a,4b. This means that the cable 100 and tip 102 stay in direct contact with the bone, preventing increased soft tissue damage, and decreasing risk of arterial injury. The tip 102 is advantageous in that it fits within the channel 6a,6b and gives the bone clamp 1 and cable 100 of the invention the mechanical property of controlling rotation of the cable 100 when in use, thus decreasing the chance of toggling of the cable 100 in unwanted planes and reducing the risk of artery perforation and/or tissue damage during use. One of the advantages of the radius of the tip 102 is that it substantially matches or is slightly smaller than the radius of the bone of interest, meaning that the tip 102 will keep tight to the curvature of the bone and will not stray into the surrounding tissue. Another advantage of the radius of the tip 102 substantially matching or being slightly smaller than the bone of interest is that it ensures that the distal end of the cable tip 102 enters the open end 8a and subsequently the channel 6a. Another advantage is that the length of the tip 102 allows the distal end of the tip 102 to pass from one jaw of the head 20 to the other jaw of the head 20 and exit through opening 7a, while keeping the trailing elements such as the proximal end of the tip 102 and the cable 100 constrained within the channels 6a,6b. This thus restrains the plane of rotation of the tip 102 as it passes from one channel to the other in the head 20. The cable tip 102 is pre-contoured to match the curvature of the bone.

The cable tip 102 is long enough such that at the moment when the distal end of the tip 102 is passing into the receiving jaw of the head 20, the rear portion of the tip 102 is still being laterally (and directionally) restrained within the other jaw of the head 20. The optimal arc length of the tip 102 is between about 5 mm and 100 mm when using a (typical femur mid-shaft) diameter of curvature of a bone of between 20 mm to 30 mm. The optimal arc length is between 15 mm and 55 mm.

The tip 102 further comprises an end point 102a. The end point 102a typically has bevelled edges 202a,202b and sides 202c,202d (see FIG. 7B). The shape of the end point 102a aims to prevent snagging on in the channels 6a,6b during passage and to prevent snagging on the bone during passage. The shape of the bevelled edges 202a,202b and the sides 202c,202d of the end point 102a match the cross-sectional shape of the openings 7b,8a to create a funnel-like effect of guiding the tip 102 into the centre of the channel 6a,6b.

The tip 102 further comprises an uncurved portion 102b, situated between the cable body 101 and the tip 102. The uncurved portion 102b allows the user to have a stiffened element of the cable that they can use to manoeuvre the cable 100 safely in a space beside the bone. The length of uncurved portion 102b will be long enough so that there is a stiffened portion long enough to be passed all the way from one jaw 4a,4b to the other jaw 4a,4b. The uncurved portion 102b may have varying stiffnesses along its length. The tip 102 is curved between the end of the uncurved portion 102b and the tip of the bevelled end point 102a.

The cable body 101 has a tensile strength of between 175 ksi (kilopound per square inch) to 280 ksi. The material used for the tip 102 may be chosen based in part on the desired stiffness of the tip 102. For example, a suitable material might be annealed stainless steel or surgical grade malleable titanium, a less malleable material such as cobalt-chrome, or another biocompatible material or alloy as needed. The diameter or cross-sectional area of the stiffened tip 102 will also affect the stiffness of the tip 102, with an increased cross-sectional area resulting in a stiffer tip 102.

In use, the tip 102 of the cable 100 is inserted into the opening 7b, through the channel 6b so that the tip 102 exits the opening 8b and enters the opening 8a. The cable 100 is then fed through the channel 6a and exits the opening 7a. A crimp is then applied. It should be understood that the reverse may also occur where the cable 100 is inserted into the opening 7a, through the channel 6a so that the cable 100 exits the opening 8a and enters the opening 8b. The tip 102 of the cable 100 is then fed through the channel 6b and exits the opening 7b. A crimp is then applied.

A cable tensioner is then used in the regular manner, that is, the free end (or ends) of the cable that has been applied to the bone is then passed through a cable tensioner. This tensioner then applies tension to the cable that is wrapped around the bone and fracture. The cable 100 can easily be attached without removing the bone clamp 1,200,300. Once the desired tension is achieved, (typically between 20 kg and 50 kg but may be more or less in certain circumstances e.g. osteoporosis), the crimp is crimped (locked) with the bone clamp 1,200,300 still in situ. Alternatively, the tensioner can be left in situ and the bone clamp 1,200,300 removed, followed by crimping. The cable 100 is cut, the bone clamp 1,200,300 is removed and the cable 100/crimp remain on the bone, while keeping the fracture reduced.

The cable 100 may have markings to indicate depth of insertion. The advantage to this is to indicate to the user the point at which they should have received the exiting cable tip 102 from channel 6a and may alert the user to desist from pushing the rear of the cable 100 and investigate the location of the cable tip 102.

A further embodiment of the cable involves a multifilament cable that has a curved tip portion with a curvature that is slightly smaller than the diameter of the bone it will encircle, with the curved tip being also a multifilament cable. The transition between uncurved and curved cable in this embodiment may be continuous in braiding or may be separated by a transitional area as described above (glue, weld, thread, snap fit etc)

The bone clamp 1,200,300, the cable 100, the tensioner, the crimper and crimp are all applied in a single plane. This allows for minimally invasive surgery. This makes for more concentrated operating by the user with better economy of movement. This may remove the necessity for the use of a separate incision-spreading instrument such as a retractor.

Some of the advantages of the bone clamp 1,200,300 of the present invention is that there is less risk to the femoral artery because it removes the need for a separate pass behind the femur into a dangerous area or blind spot, that is, the area inside of the thigh which is not visible to the user, where a number of large vessels, including the femoral artery, are located. There is less tissue damage because the configuration of the jaws 4a,4b of the clamp 1,200,300 prevents soft tissue stripping from the bone that is witnessed when using, and preparing for the use of, other cable passers.

When using the bone clamp 1,200,300 described herein, there are less surgical steps and fewer surgical tools used due to omitting the need for a cable passer. Without having to use a clamp and cable passer separately, the bone clamp 1,200, 300 described herein provides enhanced stability and ease in reduction when compared to the clamp and cable passer method of the prior art. This equates to less time in the theatre, thus providing time savings for surgeons and theatre resources. The configuration of the jaws 4a,4b of the bone clamp 1,200,300 provides the surgeons with a mechanically advantageous fixation location, allowing for ideal placement of the cable 100, especially in short/oblique fractures.

The problem with using the clamps and cable passers of the prior art methods is that the cables cannot be placed on the optimal fixation location when there is a clamp already in the way. The clamp occupies the optimal location for fixation. The problem is that these cables have been designed with a cerclage passer in mind that is separate to the clamp. Some of the advantages of the cable 100 is that it can be placed in the optimal location without having to move the bone clamp 1,200,300 that is holding the bone in the optimal place for fixation. Another advantage of the cable 100 is that it can be used/combined with the bone clamp 1,200,300 to eliminate the need for a separate cable passer. The lack of a separate cable passer means that there is less stripping of tissue from the bone. The larger the cross-sectional area of the passer (and clamp) the more tissue stripping is necessary around the bone. The higher the number of tools that need to be passed around the bone, the more tissue stripping is necessary around the bone. Thus, if the separate cable passer is eliminated, one should expect 50% less tissue stripping as the cable passer and clamp would have the same or similar cross-sectional area.

The typical radius of curvature of a typical cable passer is generally twice that of the bone it is being used on, whereas the radius of curvature of the tip of the claimed cable is similar to that of the bone being clamped. The claimed cable with the stiffened and curved tip would not typically be useable with a standard cable passer as the radius of the curvatures of either the cable or the jaws of the cable passer would not match. As a consequence, the mismatch would cause the cable tip to become wedged within the generic cable passer. Thus, the claimed cable is only suitable to be used with the claimed clamp.

In the specification the terms "comprise, comprises, comprised and comprising" or any variation thereof and the terms "include, includes, included and including" or any variation thereof are considered to be totally interchangeable and they should all be afforded the widest possible interpretation and vice versa.

The invention is not limited to be right-handed or left-handed. The channel 6*a* of the jaw 4*a* can be to the right or the left of the central part 3*a*. The channel 6*b* of the jaw 4*b* can be to the right or the left of the central part 3*b*.

The invention is not limited to the embodiments hereinbefore described but may be varied in both construction and detail.

The invention claimed is:

1. A bone clamp (1,200,300) for use in fixation of a fractured bone or prevention of fracture of a bone, the clamp (1,200,300) comprising a pair of handles (2*a*,2*b*) joined together at a pivot point (5), the handles (2*a*,2*b*) each having an arcuate jaw (4*a*,4*b*), each arcuate jaw (4*a*,4*b*) comprising a first end (7*a*,7*b*) having an opening at a proximal end (12*a*, 12*b*) of the jaw (4*a*,4*b*) in communication with a second end (8*a*,8*b*) having an opening at a distal end (14*a*, 14*b*) of the jaw (4*a*,4*b*), the first end (7*a*, 7*b*) and second end (8*a*,8*b*) in communication via a channel (6*a*,6*b*), in which the channel (6*a*,6*b*) is configured to accommodate a cable, a wire, a suture, a band or other suitable flexible material, and characterised in that the channel (6*a*,6*b*) is open continuously along its entire length and which runs uncovered continuously along its entire length through an internal face (10*a*, 10*b*) of each arcuate jaw (4*a*,4*b*), wherein the channel (6*a*) is not covered by the surface of the internal face (10*b*) and the channel (6*b*) is not covered by the surface of the internal face (10*a*) when the arcuate jaws (4*a*,4*b*) are in an engaged position intended to engage a bone, and wherein the channel (6*a*,6*b*) of the arcuate jaws (4*a*,4*b*) substantially forms an ellipse along its entire length when the arcuate jaws (4*a*,4*b*) are in the engaged position intended to engage a bone.

2. The bone clamp (1,200,300) of claim 1, wherein at least one of the second ends (8*a*, 8*b*) is flared.

3. The bone clamp (1,200,300) of claim 1, wherein at least one of the first ends (7*a*, 7*b*) is flared.

4. The bone clamp (1,200,300) according to claim 1, wherein at least one internal face (10*a*, 10*b*) comprises a plurality of ridges (12) running perpendicular to the channel (6*a*,6*b*).

5. The bone clamp (1,200,300) according to claim 1, wherein the arcuate jaws (4*a*,4*b*) have an arc measuring between 11.25° and 270°.

6. The bone clamp (1,200,300) according to claim 1, wherein the handles (2*a*,2*b*) can slide relative to each other in the same plane at the pivot point (5) where central parts (3*a*,3*b*) of the handles (2*a*,2*b*) are connected together via a coupling connector (18) and a slot (16).

7. The bone clamp (1,200,300) according to claim 1, wherein at least one channel (6*a*,6*b*) is inclined at an angle of between about 0.01° to about 45° relative to the central line of the corresponding arcuate jaw (4*a*,4*b*).

8. The bone clamp (1,200,300) according to claim 1, wherein only one channel (6*a*) is inclined at an angle of between about 0.01° to about 45° relative to the central line of the corresponding arcuate jaw (4*a*).

9. The bone clamp (1,200,300) according to claim 1, further comprising a ledge (201) extending outwards from an inside face (202) of one jaw (4*b*) between the first end (7*b*) and a central part (3*b*) of one of the pair of handles (2*b*).

10. The bone clamp (1,200,300) according to claim 1, further comprising a retractable sleeve (401) extending from the distal end (14*b*) of one jaw to the distal end (14*a*) of the other jaw.

11. A cable (100) for use with a bone clamp (1,200,300) in fixation of a fractured bone or prevention of fracture of a bone, the bone clamp (1,200,300) comprising a pair of handles (2*a*,2*b*) joined together at a pivot point (5), the handles (2*a*,2*b*) each having an arcuate jaw (4*a*,4*b*), each arcuate jaw (4*a*,4*b*) comprising a first end (7*a*, 7*b*) having an opening at a proximal end (12*a*, 12*b*) of the jaw (4*a*,4*b*) in communication with a second end (8*a*,8*b*) having an opening at a distal end (14*a*, 14*b*) of the jaw (4*a*,4*b*), the first end (7*a*, 7*b*) and second end (8*a*,8*b*) in communication via a channel (6*a*,6*b*), in which the channel (6*a*,6*b*) is configured to accommodate said cable, a wire, a suture, a band or other suitable flexible material, and characterised in that the channel (6*a*,6*b*) is open continuously along its entire length and which runs uncovered continuously along its entire length through an internal face (10*a*, 10*b*) of each arcuate jaw (4*a*,4*b*), wherein the channel (6*a*) is not covered by the surface of the internal face (10*b*) and the channel (6*b*) is not covered by the surface of the internal face (10*a*) when the arcuate jaws (4*a*,4*b*) are in an engaged position intended to engage a bone, and wherein the channel (6*a*,6*b*) of the arcuate jaws (4*a*,4*b*) substantially forms an ellipse along its entire length when the arcuate jaws (4*a*,4*b*) are in the engaged position intended to engage a bone; wherein the cable (100) comprises a body (101) and a tip (102), characterised in that the tip (102) is stiffened and has a bevelled end point (102*a*), wherein the tip (102) is curved, and wherein the tip (102) has a cross-sectional shape adapted to engage with the channel (6*a*,6*b*) of the bone clamp (1,200, 300) having a similar cross-sectional shape.

12. The cable (100) according to claim 11 for use with the bone clamp (1,200,300), wherein the bevelled end point (102*a*) further comprises edges (202*a*,202*b*) and sides (202*c*, 202*d*) that are adapted to match the cross-sectional shape of the opening at the first end (7*b*) and the opening at the second end (8*a*) of the bone clamp (1,200,300).

13. The cable (100) according to claim 11 for use with the bone clamp (1,200,300), wherein the tip (102) further comprises an uncurved portion (102*b*) between the cable body (101) and the tip (102), and wherein the tip (102) is curved between the uncurved portion (102*b*) and the bevelled end point (102*a*).

14. The cable (100) according to claim 11 for use with the bone clamp (1,200,300), wherein the tip (102) further comprises an uncurved portion (102*b*) between the cable body (101) and the tip (102), and wherein the tip (102) is curved between the uncurved portion (102*b*) and the bevelled end point (102*a*), and curved portion between the uncurved portion (102*b*) and the bevelled end point (102*a*) of the tip (102) has an arc that matches that of an arc of the arcuate jaws (4*a*,4*b*) of the clamp (1,200,300).

15. The cable (100) according to claim 11 for use with the bone clamp (1,200,300), wherein the tip (102) has an arc measuring between 11.25° and 270°.

16. The cable (100) according to claim 11 for use with the bone clamp (1,200,300), wherein the curvature diameter of the tip (102) is configured to be slightly larger to being no more than 50% smaller than the diameter of a bone being clamped.

17. The cable (100) according to claim 11 for use with the bone clamp (1,200,300), wherein the curvature diameter of the tip (102) is configured to be no more than 50% smaller than the diameter of a bone being clamped.

18. The cable (100) of claim 11 for use with the bone clamp (1,200,300), wherein the tip (102) is fixed to the body (101) of the cable (100) by welding, gluing, snap-fit, threaded or male to female connections.

19. The cable (100) according to claim 11 for use with the bone clamp (1,200,300), wherein the tip (102) has a cross-sectional shape selected from a square, a rectangle, a tri-angle, an ellipse, a pentagon, a hexagon, a heptagon, an octagon, a star shape, substantially flat, oval, flattened with rounded edges, or combinations thereof.

20. A method for fixing a fracture or preventing fracture of a bone, the method comprising:

affixing a bone clamp (1,200,300) comprising a pair of handles (2*a*,2*b*) joined together at a pivot point (5), the handles (2*a*,2*b*) each having an arcuate jaw (4*a*,4*b*), each arcuate jaw (4*a*,4*b*) comprising a first end (7*a*, 7*b*) having an opening at a proximal end (12*a*, 12*b*) of the jaw (4*a*,4*b*) in communication with a second end (8*a*,

8*b*) having an opening at a distal end (14*a*, 14*b*) of the jaw (4*a*,4*b*), the first end (7*a*,7*b*) and second end (8*a*,8*b*) in communication via a channel (6*a*,6*b*), in which the channel (6*a*,6*b*) is configured to accommo-date a cable, a wire, a suture, a band or other suitable flexible material, and characterised in that each channel (6*a*,6*b*) is open continuously along its entire length and which runs uncovered continuously along its entire length through an internal face (10*a*, 10*b*) of each arcuate jaw (4*a*,4*b*) to a bone to reduce a bone fracture or prevent a fracture wherein the channel (6*a*) is not covered by the surface of the internal face (10*b*) and the channel (6*b*) is not covered by the surface of the internal face (10*a*) when the arcuate jaws (4*a*,4*b*) are in an engaged position intended to engage a bone, and wherein the channel (6*a*,6*b*) of the arcuate jaws (4*a*,4*b*) substantially forms an ellipse along its entire length when the arcuate jaws (4*a*,4*b*) are in the engaged position intended to engage a bon;

passing a cable (100) comprising a body (101) and a tip (102), characterised in that the tip (102) is stiffened and has a bevelled end point (102*a*), wherein the tip (102) is curved, and wherein the tip (102) has a cross-sectional shape adapted to engage with the channel (6*a*,6*b*) of the bone clamp (1,200,300) having a similar cross-sectional shape through the channels (6*a*,6*b*) of the bone clamp (1,200,300);

applying a crimp to the cable (100);

tightening the cable (100); and crimping the crimp to fasten the cable (100) in place.

\* \* \* \* \*